(12) United States Patent
Ronnander et al.

(10) Patent No.: US 11,534,589 B2
(45) Date of Patent: Dec. 27, 2022

(54) IONTOPHORETIC MICRONEEDLE DEVICE

(71) Applicants: LTS LOHMANN THERAPIE-SYSTEME AG, Andernach (DE); NEW JERSEY INSTITUTE OF TECHNOLOGY, Newark, NJ (US)

(72) Inventors: James Paul Ronnander, Mount Vernon, NY (US); Laurent Simon, Somerset, NJ (US)

(73) Assignees: LTS Lohmann Therapie-Systeme AG, Andernach (DE); New Jersey Institute of Technology, Newark, NJ (US)

(*) Notice: Subject to any disclaimer, the term of this patent is extended or adjusted under 35 U.S.C. 154(b) by 0 days.

(21) Appl. No.: 16/646,626

(22) PCT Filed: Sep. 12, 2018

(86) PCT No.: PCT/EP2018/074583
§ 371 (c)(1),
(2) Date: Mar. 12, 2020

(87) PCT Pub. No.: WO2019/053051
PCT Pub. Date: Mar. 21, 2019

(65) Prior Publication Data
US 2020/0206489 A1    Jul. 2, 2020

Related U.S. Application Data

(60) Provisional application No. 62/557,473, filed on Sep. 12, 2017.

(51) Int. Cl.
| | |
|---|---|
| *A61M 37/00* | (2006.01) |
| *A61N 1/04* | (2006.01) |
| *A61N 1/32* | (2006.01) |

(52) U.S. Cl.
CPC ......... *A61M 37/0015* (2013.01); *A61N 1/044* (2013.01); *A61N 1/325* (2013.01); *A61M 2037/0007* (2013.01); *A61M 2037/0023* (2013.01); *A61M 2037/0046* (2013.01); *A61M 2037/0053* (2013.01); *A61M 2037/0061* (2013.01)

(58) Field of Classification Search
None
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |

(Continued)

FOREIGN PATENT DOCUMENTS

WO    WO-2009124096 A1    10/2009

OTHER PUBLICATIONS

Ahn et al. Where do triptans act in the treatment of migraine? Pain, May 2005; 115 (1-2) (Year: 2005).*

(Continued)

*Primary Examiner* — Melissa S Mercier
(74) *Attorney, Agent, or Firm* — Faegre Drinker Biddle & Reath LLP

(57) ABSTRACT

A medical drug devices for transdermal drug delivery systems (TDDS) comprising a novel iontophoretic polymeric microneedle device and its use in administration of drugs.

15 Claims, 8 Drawing Sheets

(56) References Cited

U.S. PATENT DOCUMENTS

| | | | |
|---|---|---|---|
| 5,011,681 | A | 4/1991 | Ciotti et al. |
| 7,226,439 | B2 | 6/2007 | Prausnitz et al. |
| 7,437,189 | B2 | 10/2008 | Matsumura et al. |
| 8,900,180 | B2 * | 12/2014 | Wolter .............. A61M 37/0015 604/46 |
| 2005/0245594 | A1 * | 11/2005 | Sutter ..................... A61M 5/46 514/419 |
| 2008/0262416 | A1 * | 10/2008 | Duan ................... A61K 9/0021 604/46 |
| 2009/0082713 | A1 | 3/2009 | Friden |
| 2014/0316333 | A1 * | 10/2014 | Kwon ..................... A61P 23/02 424/443 |

OTHER PUBLICATIONS

Ahn et al. Where do triptans act in the treatment of migraine? Pain, May 2005; 115 (1-2): 1-4 (Year: 2005).*

Pandey et al. (Current Advancement in Transdermal Biosensing and Targeted Drug Delivery, Sensors 2019, 19, 1028) (Year: 2019).*

Lahiji et al. (A patchless dissolving microneedle delivery system enabling rapid and efficient transdermal drug delivery, Scientific Reports, Jan. 21, 2015). (Year: 2015).*

Kim et al. (Microneedles for drug and vaccine delivery, Adv. Drug Delivery Rev, Nov. 2012; 64(14): 1547-1568). (Year: 2012).*

McGrath et al. (Production of dissolvable microneedles using an atomized spray process: Effect of microneedle composition on skin penetration, European Journal of Pharmaceutics and Biopharmaceutics 86 (2014) 200-211). (Year: 2014).*

Bediz et al. (Dissolvable Microneedle arrays for Intradermal Delivery of Biologies: Fabrication and Application, Pharm Res. Jan. 2014; 31(1):117-135) (Year: 2014).*

Allen et al. (Dissolvable microneedle fabrication using piezoelectric dispensing technology, International Journal of Pharmaceutics 500 (2016) 1-10). (Year: 2016).*

Dillon et al. (Formulation and characterization of dissolving microneedles for delivery of therapeutic peptides, International Journal of Pharmaceutics, 526(2017)125-136) (Year: 2017).*

Thakur et al. (Rapidly dissolving polymeric microneedles for minimally invasive intraocular drug delivery, Drug Delivery and Translational Research 6, 800-815 (2016)). (Year: 2016).*

International Preliminary Examination Report for PCT/EP2018/074583 dated Oct. 10, 2019.

International Search Report for PCT/EP2018/074583 dated Jan. 7, 2019.

Written Opinion of the International Searching Authority for PCT/EP2018/074583 dated Jan. 7, 2019.

* cited by examiner

IONTOPHORETIC MICRONEEDLE DEVICE

CROSS-REFERENCE TO RELATED APPLICATIONS

This application is a national stage application (under 35 U.S.C. § 371) of PCT/EP2018/074583, filed Sep. 12, 2018, which claims benefit of U.S. Application No. 62/557,473, filed Sep. 12, 2017, both of which are incorporated herein by reference in their entirety.

BACKGROUND OF THE INVENTION

The present invention is in the field of medical drug devices and concerns transdermal drug delivery systems (TDDS). Provided is a novel iontophoretic microneedle device and its use in administration of drugs via transdermal delivery drugs for prophylaxis and therapy.

Oral administration of biological and pharmaceutical drug products is limited by poor drug absorption and/or first pass effect metabolism in gastrointestinal tract or liver. The most common alternative is drug administration through subcutaneous/intramuscular injections or intravenous infusion. However, the use of hypodermic needles has several drawbacks including the pain associated with injection, required trained personnel to administer drug, cost of drugs and sterility. Another disadvantage is that these drug administration routes (except for intravenous infusion) lead to fluctuations in concentration of drug in blood plasma which can lead to toxic effects or ineffective treatment.

For example, sumatriptan succinate or sumatriptan, one very attractive active pharmaceutical ingredient (API), is considered the gold standard in prescription anti-migraine therapy. Currently, sumatriptan is delivered in several dosage forms, including intranasal and oral, but also subcutaneous and iontophoretic means. However, each method has its own limitation that may greatly reduce the patient's willingness to comply with the treatment. For example, the subcutaneous injection is difficult to administer when an individual is already incapacitated by a migraine headache. Oral tablet and nasal spray generally have low bioavailability of not more than 15% and 14%, respectively, and are likely accompanied by side effects of nausea and vomiting.

An attractive minimally invasive alternative may be the use of transdermal systems (TDDS), so called transdermal patches, which can be self-administered and allow to deliver drugs through the skin in a controlled and yet reliable rate. Transdermal technology is currently limited to APIs of small, lipophilic molecules due to the skin's strong epidermal barrier. Several physical and chemical permeation methods, e.g. chemical enhancers, iontophoresis or microneedles, have been studied to increase diffusion and drug uptake through the skin. These methods mostly aim to disrupt the lipid bilayer structure of the skin's stratum corneum to increase permeation and promote the systemic absorption of drug. These methods have shown promise in lab studies but yield limited clinical and commercial success.

Microneedles (MNs) were developed as minimally invasive transdermal systems and are expected to also deliver APIs of macromolecules or hydrophilic compounds through the skin. Such microneedles can effectively bypass the stratum corneum and epidermis and reach beyond it to achieve systemic uptake of drug in the underlying dermis. They are normally designed with an array of micro sized needles used to puncture the epidermis with micron-sized 'holes' and create channels for the drug to flow into directly into the underlying dermis which is rich of capillaries and provide for instant systemic circulation of the drug.

The individual microneedles are designed with heights of approx. 50 to 900 µm and a surface density of approx. 2000 needles/$cm^2$ or less. These dimensions allow the needles to puncture and penetrate the stratum corneum and dermis, but not to extend to nerve fibers and blood vessels.

Known microneedles are fabricated from materials such as silicon, metal or polymer and are formed in geometries such as cones, pyramids or cylinders, and arranged in arrays of circular, triangular or square shape.

Currently, five different types of microneedle arrays (MNs) are under development: solid MNs, coated MNs, dissolvable MNs, hollow MNs, and hydrogel MNs. For example, influenza vaccination using hollow MNs is currently in widespread clinical use.

Dissolving microneedles (DMN) are made of water-soluble biodegradable polymers that incorporate the API within the microneedle array. The needles are inserted into the epidermis where they dissolve in minutes, releasing the API into the skin and dermis layers for rapid distribution into the body fluid. No sharp medical waste is left for disposal after use. It has been shown that the skin punctures, created in the process, are painless and heal within 3 days.

The combination of iontophoresis and microneedle technologies has been shown to increase uptake of macromolecules through the skin while modulating the drug delivery rate. Iontophoresis is a techniques of introducing charged particles into the body through the skin by applying a local electrical current.

In vitro experiments with poly(methyl vinyl ether-maleic acid) (PMVE/Ma) microneedles loaded with a macromolecule (e.g. bovine insulin) demonstrated increased delivery through porcine skin compared to microneedle or iontophoresis alone (Garland, Martin J., et al. "Dissolving Polymeric Microneedle Arrays for Electrically Assisted Transdermal Drug Delivery." J. of Controlled Release 159(2012), 52-59). An in vitro study using maltose microneedles combined with iontophoresis on hairless rats showed a 25-fold increase in delivery of the methotrexate (Vemulapalli, V. et al. "Synergistic effect of iontophoresis and soluble microneedles for transdermal delivery of methotrexate." J. Pharm. Pharmacol. 60(2008), 27-33). Nevertheless, these combined technologies are limited and only applicable in a scale for basic research.

U.S. Pat. No. 7,226,439 Describes a microneedle device which uses hollow microneedles for delivery of drugs across biological tissue by compressing a reservoir containing drug above the microneedles.

U.S. Pat. No. 7,437,189 B2 describes an iontophoresis device capable of delivering ionizable drug of high-molecular weight to a living body using low current or voltage conditions.

US 2009/0082713 A1 describes a method where skin is microporated using microneedle device and then, following microporation, a peptide molecule is administered through microporated skin using iontophoresis.

SUMMARY OF THE INVENTION

A novel iontophoretic polymeric microneedle array device is provided for the transdermal delivery of bio macromolecules or drug macromolecules through the skin. The microneedle array is comprised of a dissolving biodegradable, soluble polymeric solutions containing encapsulated molecules.

The device will eliminate deficiencies inherent in either technology. For example, the microneedle systems have an inherent lag time prior to patient receiving therapeutic effect. Application of an electrical current through iontophoresis increases drug diffusion to reduce lag effect. The electrical current may then be regulated to yield a sustained therapeutic dose to patient.

Furthermore, the amount of electrical current required with the iontophoretic device is reduced. The microneedle penetrates the stratum corneum barrier reducing the total electrical energy required to force drug molecules into the dermal layer. This reduces the size of the iontophoretic device with smaller battery requirements which potentially leads to more efficient and longer treatment capabilities.

In a first aspect there is provided a polymeric microneedle array for delivery of macromolecular compounds (API) through the skin which has a plurality of micro-scaled and solid microneedles. According the invention, the microneedles consist of a dried polymer. The liquid polymer composition before drying comprises:

a water soluble polymer as a binder in an amount of 15 to 40 wt. %, preferably 20 to 30 wt. %;
a humectant/softener in an amount of less than 2 wt. %, preferably from 0.5 to 1.5 wt. %, most preferred about 1 wt.; and
a surfactant in an amount of less than 2 wt. %, preferably from 0.05 to 1.0 wt. %, most preferred about 0.1 wt.; and
the macromolecular compound (API) encapsulated therein in an amount of 1 to 15 wt. %, preferably from 5 to 10 wt. %.

In a second aspect related thereto, there is provided an active transdermal patch device, in particular a micro-iontophoretic device, for the delivery of macromolecular compounds (API) through the patient's skin. According to the invention the devices comprises:

a power supply with a controllable current source
a first skin electrode, i.e. cathode, electrically connected to the power supply, and
a second skin electrode, i.e. anode, electrically connected to the power supply, the second skin electrode, i.e. anode, comprises the polymeric microneedle array of the invention as described herein.

A third aspect is a method for the preparation of the polymeric microneedle array of the invention as described herein. The method of the invention comprises the steps of:
(a) dissolving in water:
a water soluble polymer as a binder, preferably in an amount of from 15 to 40 wt. %, more preferred from 20 to 30 wt. %;
a humectant/softener, preferably in an amount of less than 2 wt. % or from 0.5 to 1.5 wt %, most preferred of about 1 wt. %, and
a surfactant, preferably in an amount of less than 2 wt. % or from 0.05 to 1.0 wt %, most preferred of about 0.1 wt. %, and
the macromolecular compound (API), preferably in an amount of from 1 to 15 wt. %, more preferred from 5 to 10 wt. %,
to prepare a liquid polymer composition; wherein the wt. % are given with respect to the liquid polymer composition before drying;
(b) molding the liquid polymer composition in flexible molds having the negative form of the microarray to be produced;
(c) drying the polymer composition within the mold; and
(d) removing the dried polymeric microneedle array having formed solid microneedles from the mold.

A polymeric microneedle array having the macromolecular compound (API) encapsulated therein is obtained. The polymeric microneedle array is dissolvable upon contact with the skin due to the solubility of the polymeric components used.

A forth aspect of the invention is a method for the transdermal administration a macromolecular API to a patient comprising the steps of:
(a) microporating the skin of the patient by placing the polymeric microneedle array of the invention with the macromolecular API encapsulated therein onto or into the patient's skin, thereby allowing the microneedles to penetrate the stratum corneum of the skin, and
(b) applying anodic electrical current (+) through said microneedle array, such that the positively charged macromolecular API encapsulated therein is released from the microneedles into the patient's skin.

The amount of API released can be controlled by the level of anodic current (+) flowing through the microarray. For current generation a micro iontophoretic device is used.

Yet another related aspect of the invention is a method for the prophylaxis and/or therapy of migraine in a patient suffering therefrom, comprising transdermally administering sumatriptan as the macromolecular API by using the polymeric microneedle array of the invention having sumatriptan as the macromolecular API encapsulated therein and by applying the steps of the method of the fourth aspect described hereinabove.

The articles "a" and "an" are used herein to refer to one or to more than one (i.e., to at least one) of the grammatical object of the article. By way of example, "an element" means one element or more than one element.

As used herein, the term "and/or" includes any and all combinations of one or more of the associated listed items.

"About" as used herein when referring to a measurable value such as an amount, a temporal duration, and the like, indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

The above summary of the present invention is not intended to describe each disclosed embodiment or every implementation of the preset invention. The detailed description that follows more particularly exemplifies illustrative embodiments.

DETAILED DESCRIPTION OF THE INVENTION

Figure 1:
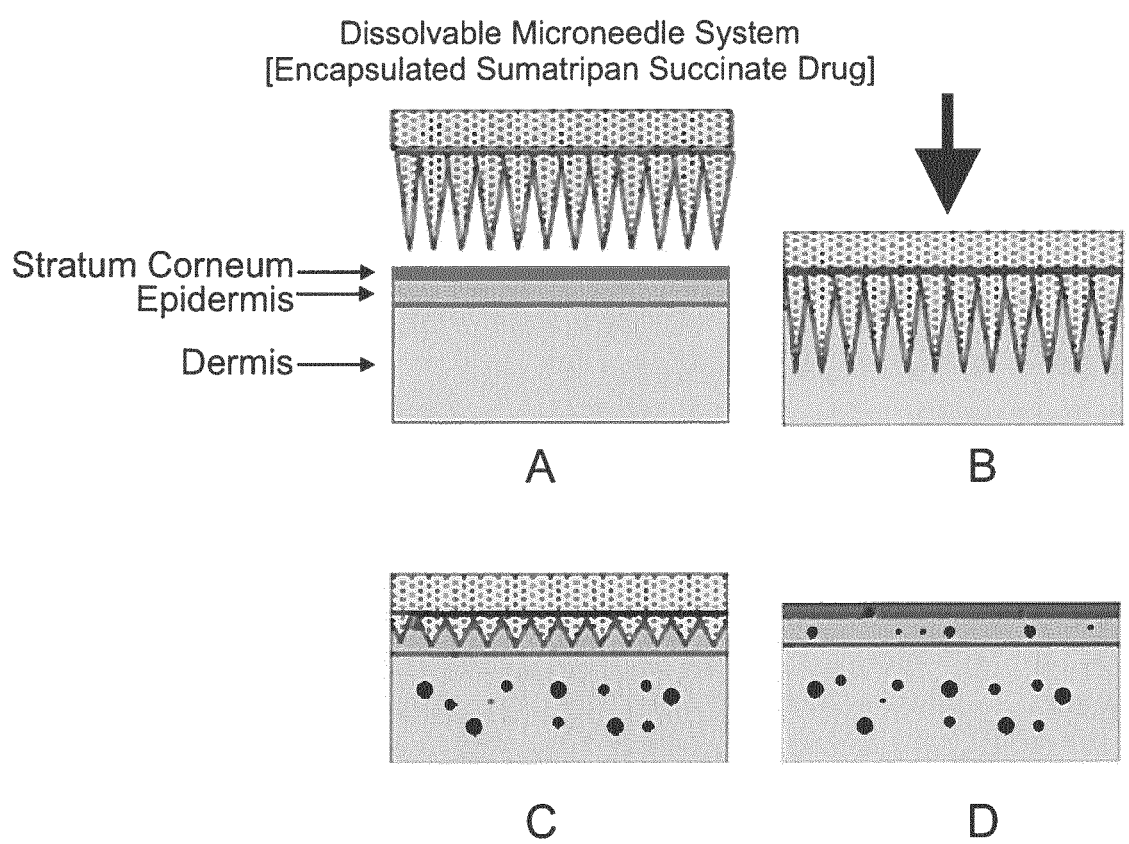
FIG. 1: Dissolvable microneedle schematic representation for rapid or controlled release of the drug encapsulated within the microneedles.

The polymeric microneedle array is prepared from a liquid polymer composition which, before drying, comprises one solvent, in particular water, a water soluble polymer as a binder, which is the main component, but also of a humectant/softener and a surfactant, the macromolecular compound (API) is encapsulated is this polymer composition. During drying of the polymer composition, most of the solvent, i.e. water, volatilizes.

It should be noted that further excipients such as buffers, pH-adjusting agents, solvents, solubilizing agents or stabilizers or the like may be present in small amounts, mainly dependent on the chemical and physical nature of the API to be included/encapsulated in the polymer composition. However, in a particular embodiment, the polymer composition is void of such other excipients, and a polymeric microneedle array is provided which consists only of the water soluble polymer the humectant/softener the surfactant, and the encapsulated macromolecular compound (API).

The microneedle array of the invention is basically comprised of a water soluble or biodegradable polymer to form solid dissolvable microneedles. Such biodegradable polymers are preferably selected from hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), poly(lactide-co-caprolactone) and the like. In a more preferred embodiment the water soluble degradable polymer is polyvinylpyrrolidon (PVP), most preferred is a medium viscosity PVP having an average molecular weight (Mw) of 30,000 to 50,000 and preferably about 40,000, generally available as PVP-K30 polymer.

A preferred humectant and softener preferably include urea, polyhydric alcohol such as glycerol (glycerin), sorbitol, xylitol, or a low molecular weight PEG, 1-2-propylene glycol, dipropylene glycol, polyethylene glycol, 1,3-butylene glycol, or 1,2,6-hexanetriol, alpha hydroxy acids, dimethicone, methyl gluceth-20, plankton extract, and mannitol. One of the preferred is glycerol.

A preferred surfactant is a nonionic surfactant or emulsifier. Nonionic surfactants include polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan.

Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560 which are incorporated by reference for emulsifiers). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. One of the preferred is polysorbate 80.

In the preferred embodiments, the drug or compound (API) encapsulated in the polymeric microneedle array is macromolecular and is hydrophilic. In more preferred embodiments, the API is selected from alkaloids, preferable neuro-active alkaloids, and mixtures thereof. Most preferred the API is anti-migraine agent sumatriptan (CAS registry number: 103628-46-2) or a derivative thereof, particularly sumatriptan succinate.

To prepare the polymeric microneedle array of the invention, it is preferred to dissolve all components of the polymer composition in the specific amounts described elsewhere herein, preferably PVP, glycerol, polysorbate 80, and the API in water as the preferred solvent. About 2 mL of the liquid polymer solution can be poured into negative molds, which are flexible and preferably made of a dried silicon elastomer. The form of microneedle array is provided by the flaible mold. The molds are dried preferably overnight and at room temperature. After drying, the solid microneedle arrays can be peeled from the molds and can be stored in sealed moisture resistant containers.

EXAMPLES

1. Chemicals and Reagents

Sumatriptan succinate [3-[2-(dimethylamino) ethyl]-N-methyl-indole-5-methane-sulfonamide succinate (1:1)] (MW=413.5) from Meohs Fine Chemicals (Iberica SL), polyvinylpyrrolidone (Kollidon K30, MW=40,000, BASF, Ludwigshafen, Germany); glycerol (glycerine) from P & G Chemicals (Cincinnati, Ohio); Polysorbate 80 from Croda (New Castle, Del.); and Nitrazine yellow from Alfa Aesar (Ward Hill, Mass.).

2. Preparation of Sumatriptan Microneedle Arrays

To prepare the soluble microneedle formulations with encapsulated sumatriptan succinate; PVP, glycerol, polysorbate 80, and sumatriptan succinate were dissolved in water to form 2.0 mL solution.

Negative molds of a platinum-cured silicon (PDMS) microneedle array were acquired from LTS Lohmann Therapie-Systeme AG (Andernach, Germany). The silicone PDMS molds were filled with PVP-sumatriptan solution using method described by Ripolin et al. ("Successful application of large microneedle patches by human volunteers." Int. J. Pharm. 521(2017), 92-101).

Next, the molds were dried overnight on benches under ambient conditions and room temperature. The dried microneedle arrays were carefully peeled from the molds and stored in sealed moisture resistant containers.

The same procedure was adopted to prepare four different PVP-sumatriptan (PVP-S) microneedle formulations. The microneedle arrays were prepared using the concentrations of PVP-S solutions listed in Table 1.

| Formulation | Sumatriptan-succinate | PVP | Glycerin | PS 80 |
| --- | --- | --- | --- | --- |
| F1 | 10.0 | 30.0 | 1% | 1% |
| F2 | 5.0 | 30.0 | 1% | 1% |
| F3 | 5.0 | 20.0 | 1% | 1% |
| F4 | 15.0 | 30.0 | 1% | 1% |

Table 1 lists the microneedle wet composition (wt. %) before drying. The DMNs contained water soluble polymer PVP as a binder, glycerol as a humectant and softener, and polysorbate 80 as a surfactant.

The sumatriptan did not fully dissolve into solution at the higher F4 formulated concentration (15 wt. %). However, F4 DMN arrays were produced to characterize the effect of higher drug concentration on DMN physical properties.

The microneedle array formulation and processing procedures were developed while considering manufacturing concerns. To this end, we focused on materials that could be mixed readily, with commonly-used mixers, to form an aqueous solution. The resulting system should be easy to degas. The hydrophilic sumatriptan succinate compound was formulated using a readily soluble, medium viscosity polyvinylpyrrolidone K30 polymer. The polymer dissolved in water and was easily degassed with slow mixing or by sitting on a benchtop.

Figure 7:
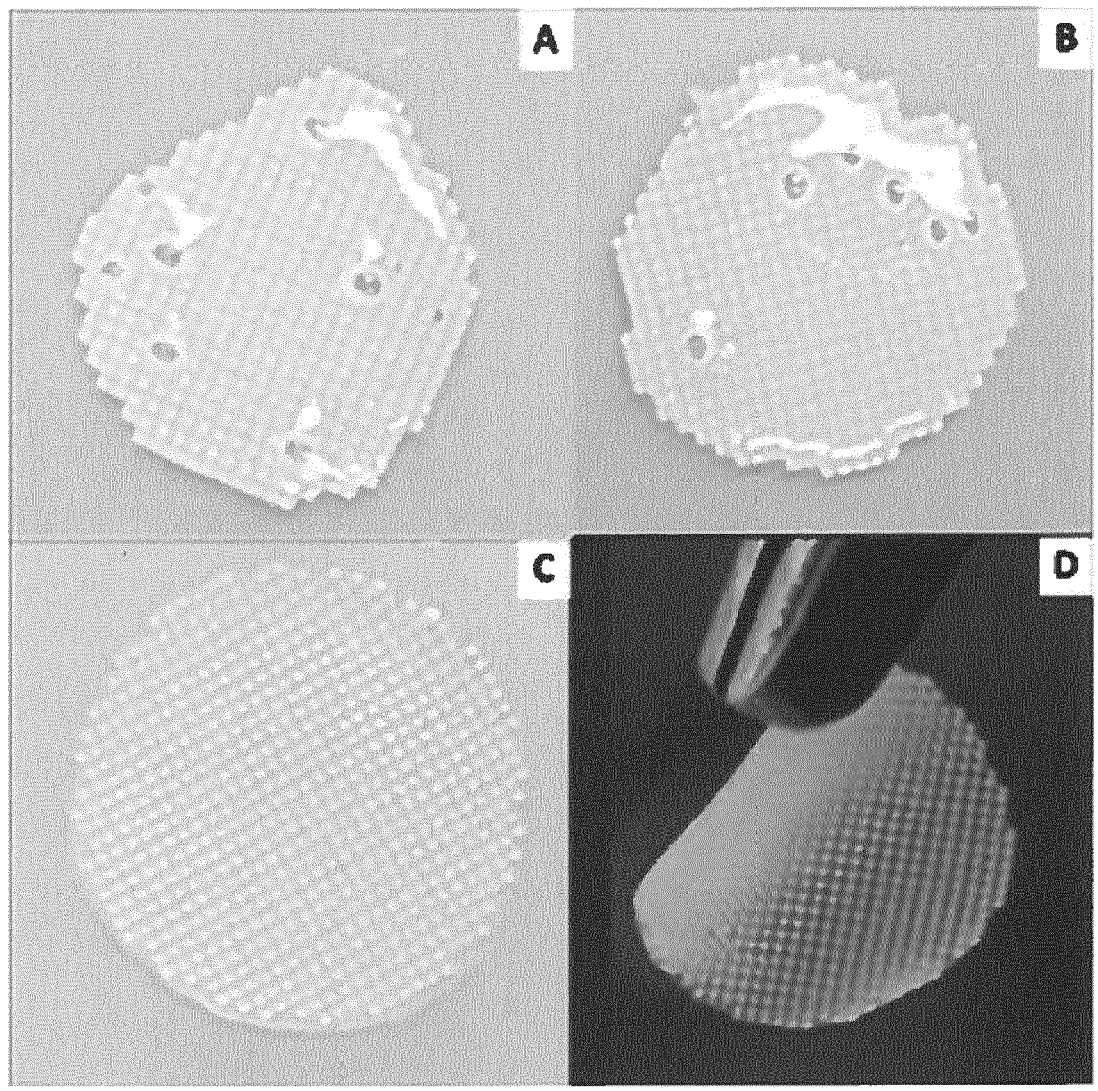
FIG. 7: (A-B) photographs of 20% PVP DMN arrays resulting in bubbles and beading effect; (C-D) photographs of formulation F3 demonstrating flexible DMN arrays without bubbles or beading effect.
Figure 8:
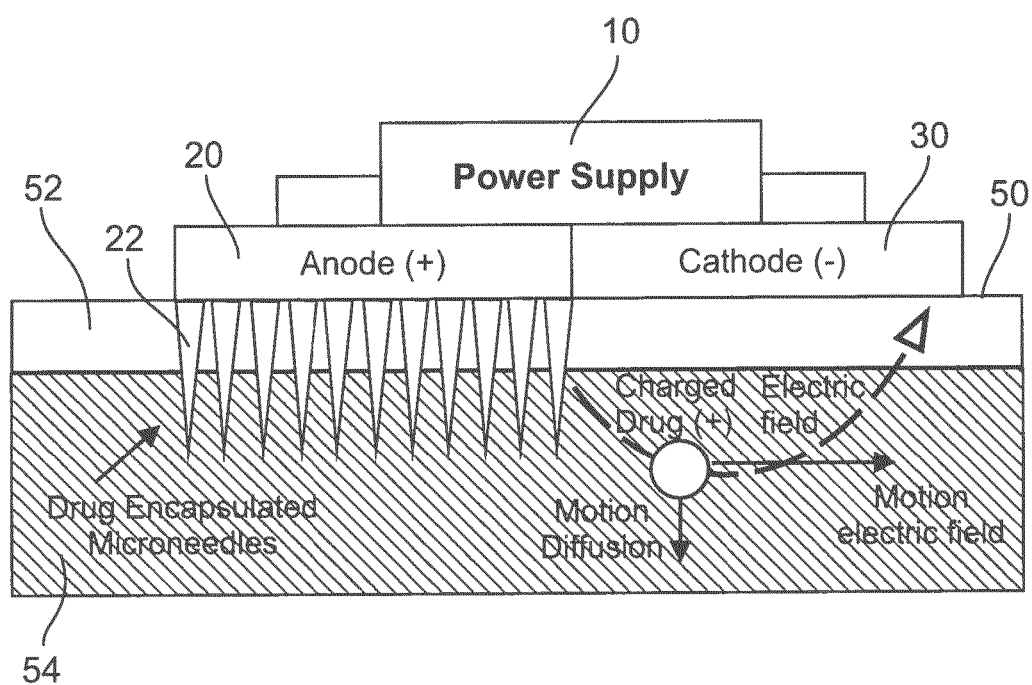
FIG. 8: A schematic drawing of a transdermal drug delivery device of the present invention, comprising a power supply (10) with a controllable current source and two skin electrodes (20, 30) each in electrical connection with the power supply (10). The cathode (30) can be brought in direct contact with a patient's skin (50). Cathodic current (−) can be applied to the skin tissue through the power supply (10) and the cathode (30). According to the invention, the anode (20) is comprised of or carries the polymeric microneedle array (22). Upon attachment of the device to the patient's skin the microneedles of the anodic microneedle array (22) can penetrate the skin and thereby reach through the stratum corneum (52) into underlying tissue of the epidermis (54). Anodic current can be applied to the skin tissue through the power supply (10) and the anode (20). Charged molecules of the API encapsulated in the polymeric microneedles are active released through electromotoric force and enter into the tissue of the epidermis (54) and eventually in the circulation of the patient.

Initial experiments formulated DMNs with 20 wt. % PVP and water resulting in glassy, brittle DMN arrays containing air bubbles. This solution displayed a high surface tension resulting in a beading effect preventing solution from fully covering DMN round molds. Polysorbate 80 was added as a surfactant to reduce surface tension and to minimize bubbling and beading effect. Glycerol was added as a humectant to retain moisture and increase flexibility for applications to non-uniform skin surfaces (FIG. 7).

3. Microscope Characterization of Microneedle Arrays

A visual characterization of the microneedle arrays was performed using light microscopes (Nikon Optiphot-2, Nikon, Japan), digital sight (Nikon D5-Fi1, Nikon Corp, Japan) and imaging software (NIS-Elements, Nikon, Japan).

Figure 2:
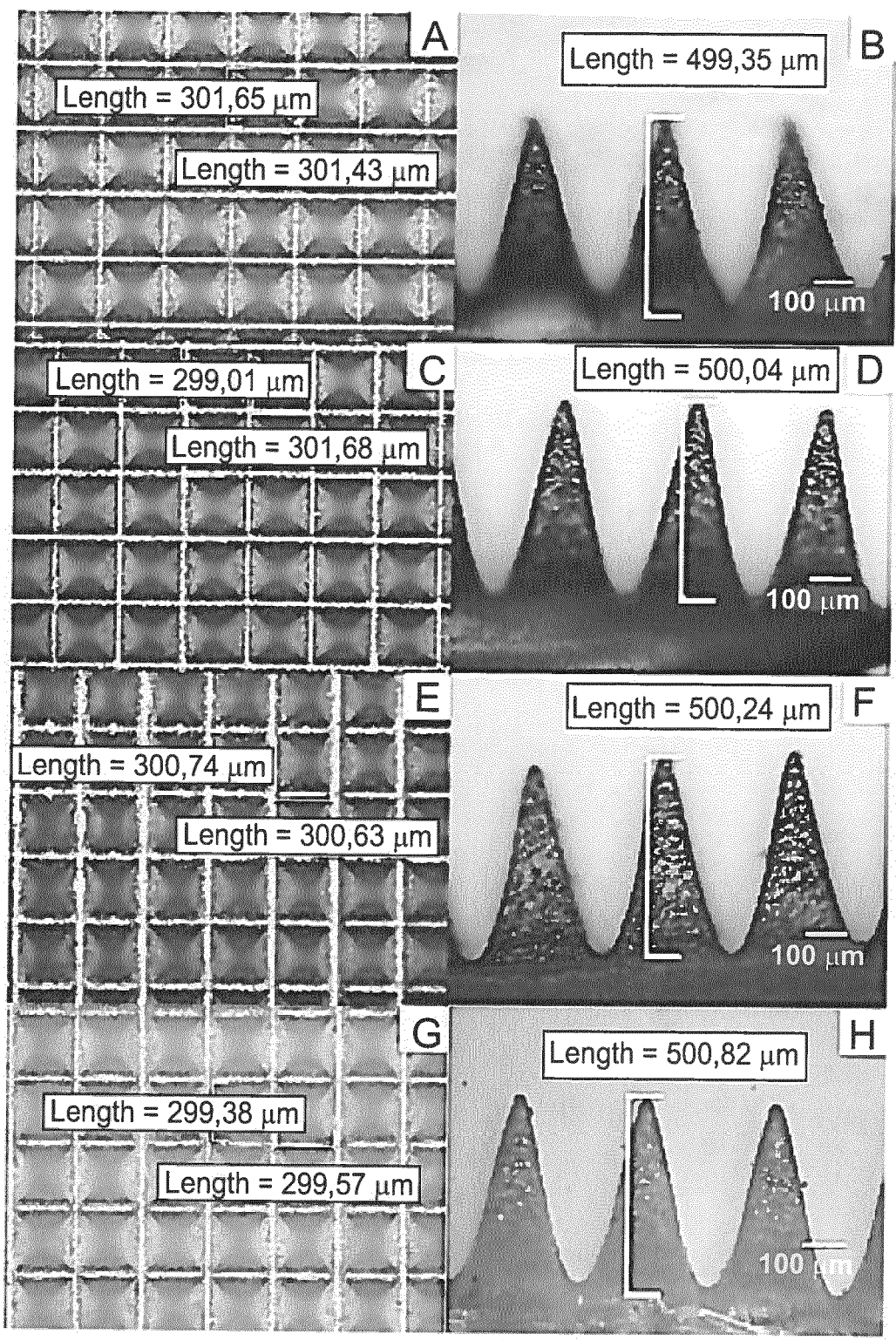
FIG. 2: Microscope images of microneedle arrays and individual needles; (A-B) F1 microneedles; (C-D) F2 microneedles; (E-F) F3 microneedles; (G-H) F4 microneedles.

All the microneedles maintained consistent appearance, shape and dimensions regardless of the PVP-S composition. Each array had an opaque, off-white appearance and contained 600 needles in a 10-mm-diameter circular region. Individual needles were in the form of a pyramid with a height of 500 µm and a base width of 300 µm. The pitch distance between DMNs (center-to-center) was 350 µm (FIG. 2).

4. Mechanical Testing of Microneedle Arrays

A tensile test machine (TA.XTPlus, Stable Microsystems Ltd, Godalming, UK) was required to assess whether DMNs are able to penetrate the skin. The mechanical failure force of microneedle arrays was measured using the instrument in compression mode fitted with a 3-point bend apparatus (HPD/3PB, Stable Microsystems Ltd, Godalming, UK). The microneedles were stored for more than 24 hours at 25° C. and 45% relative humidity before conducting the tests. Once a single microneedle array was loaded onto the stationary mount, a sensor probe applied an axial force to the DMNs at a speed of 0.1 mm/s. The test was aborted when a maximum displacement (5 mm) was attained or force decreased below the threshold (<0.1 N).

Figure 3:
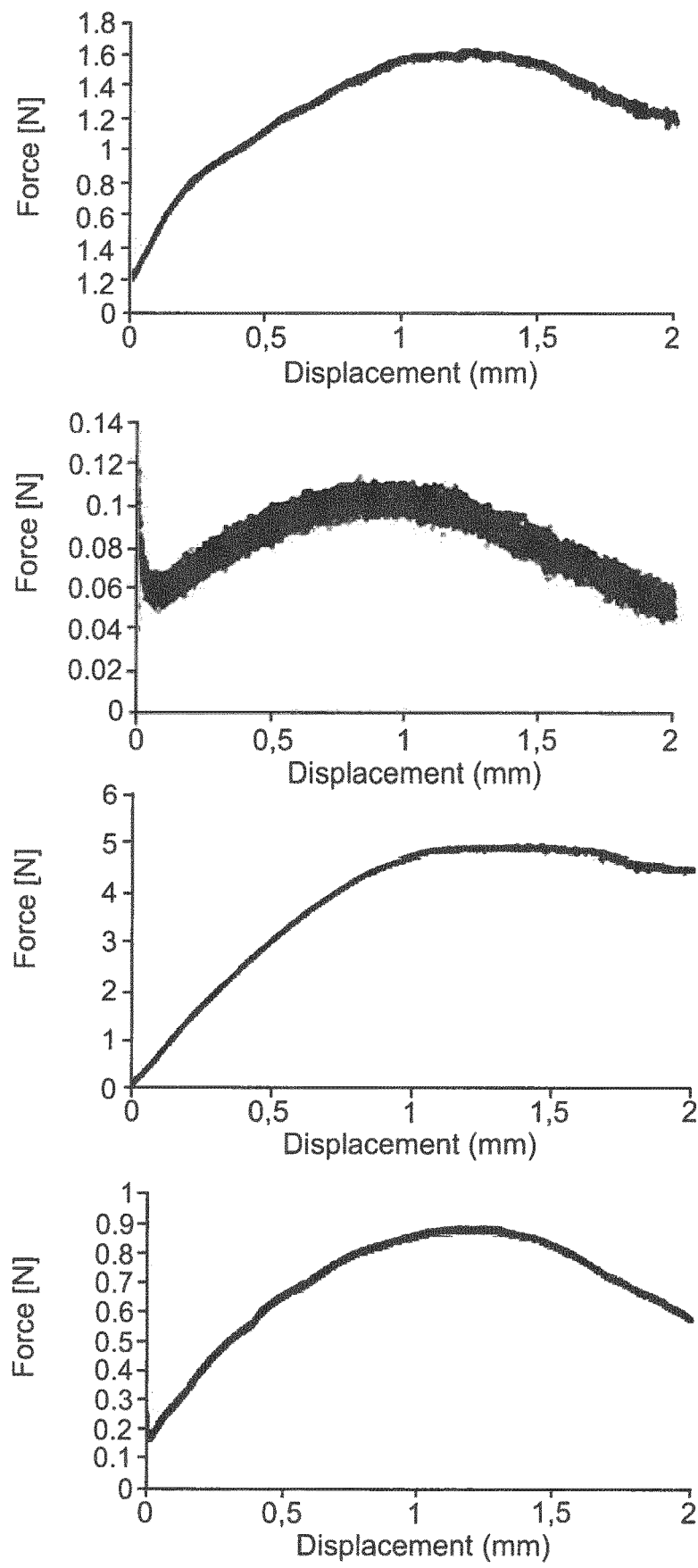
FIG. 3: Texture analyzes with 3-point bend apparatus force-displacement curves; (A) F1 microneedle; (B) F2 microneedle; (C) F3 microneedle; (D) F4 microneedle. Average values, n=3.

The mechanical behavior of the needles was determined with a texture analyzer fitted with a 3-point bend apparatus. The DMN arrays were subjected to an axial displacement of 5 mm (0.1 mm/s) to measure the failure force of a DMN. None of the DMN arrays fractured during testing. Profiles of force versus displacement (analogous to stress-strain curves), based on average force values (n=3), were generated for all formulations (FIG. 3). A light microscope was used to inspect the needles before and after mechanical testing. The applied force caused some needles to bend but not break (i.e fracture).

5. Skin Preparation and TEWL Measurement

Whole female Göttingen minipig skin tissue samples were acquired from Ellegaard Göttingen Minipigs Agricultural Service (Dalmose, Denmark). Tissues were thawed at room temperature and rinsed with water. The skin from the back of the minipig was cut to a thickness of 800 µm using an electric dermatome Acculan 3TI (Aesculap AG, Tuttlingen, Germany). The dermatomed skin was punched into 25 mm diameter samples, frozen and stored for use within a 9 month period.

Microneedle penetration can also be assessed by measuring transepidermal water loss (TEWL) with a TEWL device (Biox AquaFlux, AF200, London, UK). This evaluation was conducted on selected minipig skin samples before and after insertion of a microneedle array into the skins. For comparison, testing was also conducted before and after removal of the stratum corneum using the tape-stripping method. This technique consisted of applying standard acrylic tape of ¾" (19 mm) diameter to the stratum corneum side of the skin for 10 seconds and removing. The procedure was repeated 15 times to ensure complete removal of the stratum corneum.

The effect of microneedle application on the barrier function of the minipig skin was evaluated using transepidermal water loss (TEWL). The water loss content was used to measure the quality of minipig skin samples pre- and post-treatment using Formulation 1 (Table 2). The DMN arrays were applied to the skin and held in place for 15 seconds and then removed. This was compared to results for minipig skin before and after removal of stratum corneum using the tape-stripping method (15×).

| Sample | Skin Weight (mg) | TEWL ($g/m^2h$) | | |
|---|---|---|---|---|
| | | Pre-Treatment | Post-Treatment | Difference |
| A. Microneedle Insertion | | | | |
| 1 | 385 | 14.62 | 74.13 | 59.51 |
| 2 | 415 | 12.58 | 73.45 | 60.87 |
| 3 | 415 | 18.33 | 73.99 | 55.66 |
| Average ± SD | | 15.18 ± 2.92 | 73.86 ± 0.36 | 58.68 ± 2.70 |
| B. Tape Strip (15x) | | | | |
| 1 | 445 | 14.02 | 66.78 | 52.76 |
| 2 | 465 | 16.38 | 73.90 | 57.52 |
| 3 | 435 | 15.68 | 70.56 | 54.88 |
| Average ± SD | | 15.36 ± 1.21 | 70.41 ± 3.56 | 55.05 ± 2.38 |

Table 2 shows the results of TEWL analysis of minipig skin; (A) Before and after treatment with formulation F1 microneedle for 15 seconds; (B) Before and after tape strip (15×); average values±SD.

6. In Vitro Diffusion Studies

Experiments were conducted in vertical Franz cells (Glastechnik, Gräfenroda, Germany) with a diffusion area of 1.595 cm2. The skins were thawed and placed onto a benchtop with the stratum corneum facing up. To mimic realistic conditions, the samples were not pre-wetted with water. Previously prepared PVP-S microneedle arrays were introduced into the dermal layer using a custom device to provide standardized application conditions that applied a uniform impulse force (approximately 150 N/cm2) across the microneedle array during insertion. Following this treatment, the skin samples were gently placed into a Franz cell with the base of the DMN facing the donor compartment. The receiver cell was filled with 10 mL phosphate buffered solution (pH 7.4) (PBS) containing sodium azide (0.1%, w/w), stirred and controlled at 32° C. At predetermined intervals, the receiver solution was withdrawn completely and replaced with fresh PBS to maintain sink conditions. The drug residues, remaining in the samples after the in-vitro diffusion experiments, were extracted by shaking the skin sections for 24 hours in 5 mL of methanol.

Aliquots, withdrawn from the receiver compartment, were analyzed using a High-Performance Liquid Chromatography (HPLC) system (Jasco LC-2000Plus Series, Tokyo, Japan). The HPLC was equipped with a UV Detector (Jasco 2077) and a C18 Kromasil column (250×4.6 mm, 5 µm, VDS Optilab, Berlin, Germany). The mobile phase consisted of a mixture of sodium dihydrogen phosphate solution and acetonitrile, pH 3.2 (90:10), flowing at a rate of 1.5 mL/min. The injection volume was 20 µL and UV detection was set at 227 nm.

Figure 4:
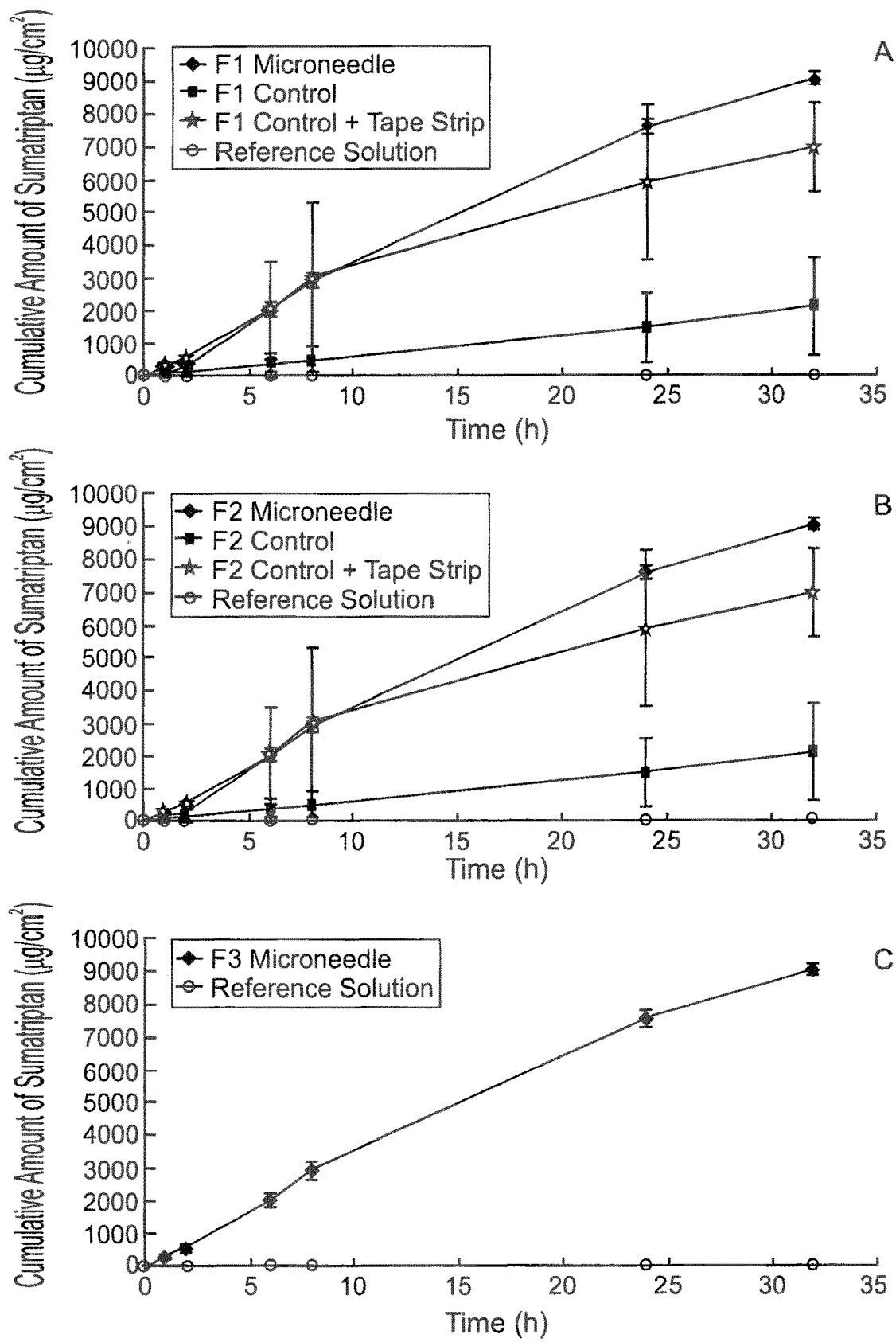
FIG. 4: Permeation profile of sumatriptan succinate (SS) loaded microneedles after 32 hours; (A) F1 microneedles, F1 control (microneedle inverted on skin), F1 control+tape strip (15×) and reference solution (5 mg/mL sumatriptan succinate); (B) F2 microneedles, F2 control, F2 control+tape strip (15×) and reference solution; (C) F3 microneedles and reference solution. Average values±SD, n=3; reference solution, n=6.
Figure 5:
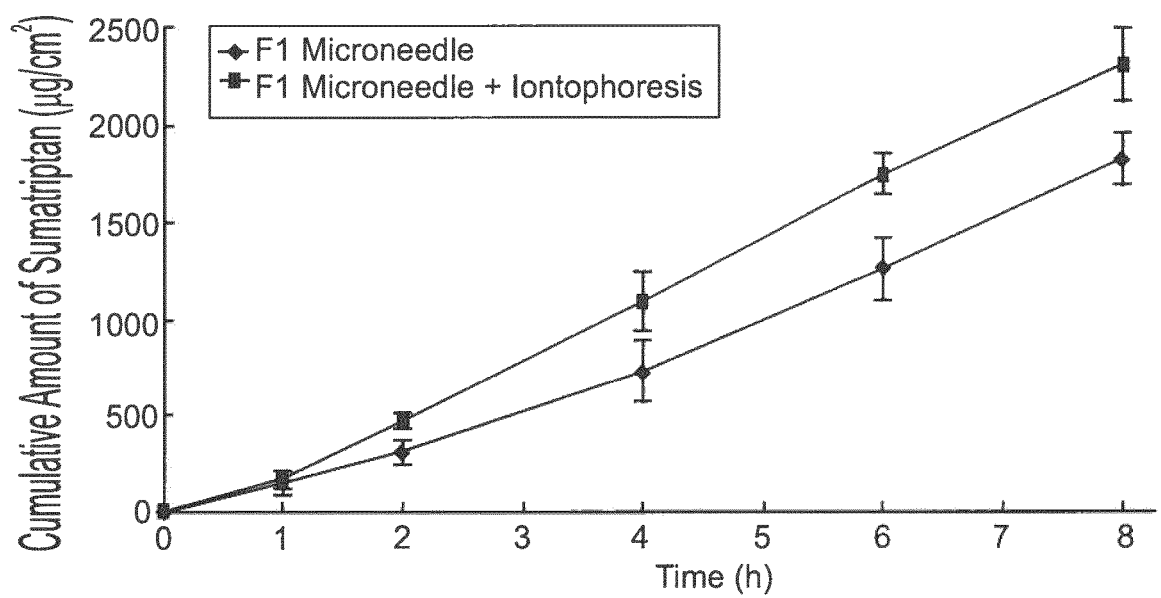
FIG. 5: Permeation profile of sumatriptan succinate (SS) loaded microneedles after 8 hours; F1 microneedle with electric current, 0.6 mA/cm^2 (Average values±SD, n=3), F1 microneedle only (Average values±SD, n=2).

Transdermal diffusion of the API across female minipig skins was measured using microneedle arrays prepared from formulations F1, F2 and F3. The cumulative amount (µg/cm2) of the drug, in all three formulations, was recorded over a 32-hour period. Passive diffusion (control) experiments were also performed for comparison with microneedle arrays (formulation F1 and F2) applied to inverted minipig skin (i.e. needles facing up). Additional passive diffusion experiments were conducted using inverted microneedle arrays (formulation F1 and F2) on minipig skin following removal of the stratum corneum by the tape-stripping method (15×). Transdermal transport from a reference donor solution, containing 5 mg/ml sumatriptan in PBS (pH 7.4), was determined (FIG. 4).

Data, including microneedle drug load (µg/cm2); cumulative amounts, Q (µg/cm2); percentage released at 24-hour; sumatriptan steady-state flux, Jss (µg/cm2 hr); sumatriptan retained in skin (µg/cm2) and lag time (hr) were recorded or calculated (Table 3). The steady-state flux and the lag time (hr) were approximated for all experiments by taking the slope of the steady-state portion of the cumulative flux curves. The steady-state flux occurred in microneedle arrays and tape-stripped inverted samples within 2 to 8 hours. It took the control and reference samples 24 to 32 hours to reach steady-state flux. The drug was extracted from the skins by dissolving samples in methanol.

| Sample | Sample Size | Drug Load ($\mu g/cm^2$) | Cumulative Amount, $Q_{24}$ ($\mu g/cm^2$) | Percentage Released in 24 h (%) |
|---|---|---|---|---|
| Reference Solution | n = 6 | 421 ± 3.4* | 15 ± 22 | 2.4 ± 3.5 |
| F1 (Control) | n = 3 | 10684 ± 192 | 1491 ± 1066 | 13.9 ± 9.9 |
| F1 (Inverted) + Tape Strip (15x) | n = 3 | 10820 ± 130 | 5904 ± 2379 | 54.7 ± 22.5 |
| F1 Microneedle | n = 3 | 11070 ± 84 | 7598 ± 223 | 68.6 ± 2.5 |
| F2 (Control) | n = 3 | 5499 ± 184 | 443 ± 388 | 8.0 ± 6.9 |
| F2 (Inverted) + Tape Strip (15x) | n = 3 | 5361 ± 89 | 3585 ± 681 | 67.0 ± 13.5 |
| F2 Microneedle | n = 3 | 5522 ± 111 | 4059 ± 179 | 73.5 ± 3.8 |
| F3 Microneedle | n = 3 | 5433 ± 161 | 4291 ± 367 | 78.9 ± 4.5 |

| Sample | Sample Size | Sumatriptan Flux, $J_{ss}$ ($\mu g/cm^2 h$) | Sumatriptan Retained in Skin ($\mu g/cm^2$) | Lag Time (h) |
|---|---|---|---|---|
| Reference Solution | n = 6 | 1.3 ± 2.0 | 56 ± 39 | 13.5 ± 3.1 |
| F1 (Control) | n = 3 | 78 ± 52 | 419 ± 250 | 6.0 ± 2.4 |
| F1 (Inverted) + Tape Strip (15x) | n = 3 | 458 ± 325 | NT | 1.5 ± 0.22 |
| F1 Microneedle | n = 3 | 395 ± 31 | 367 ± 35 | 0.65 ± 0.19 |
| F2 (Control) | n = 3 | 30 ± 24 | 419 ± 250 | 9.4 ± 1.6 |
| F2 (Inverted) + Tape Strip (15x) | n = 3 | 193 ± 86 | NT | 1.5 ± 0.16 |
| F2 Microneedle | n = 3 | 192 ± 19 | 188 ± 42 | <0.1 |
| F3 Microneedle | n = 3 | 268 ± 62 | 136 ± 120 | <0.1 |

Table 3 lists the sumatriptan succinate diffusion data for the Franz cell experiments after 32 hours; average values ±SD.

Following diffusion, the skin samples were visually inspected to determine if the microneedles were fully dissolved and had penetrated skin. It was possible to implement this procedure because an indicator (nitrazine yellow, 0.01% w/w), which appeared blue in the skin, was added to most of the microneedles. The microneedle arrays fully dissolved for formulations F1, F2, F3 and were shown to penetrate skin.

Figure 6:
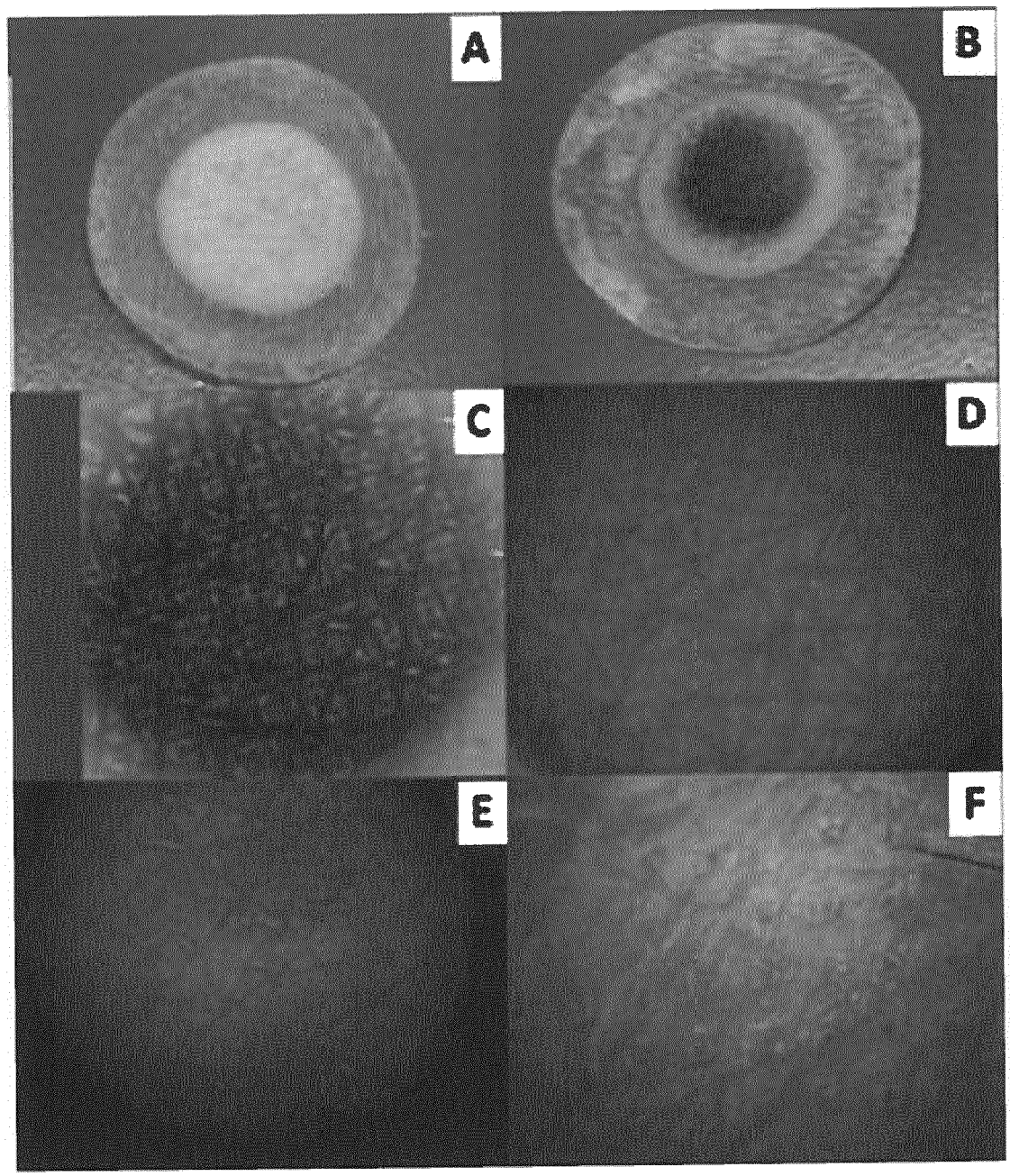
FIG. 6: Photographs and microscope images of minipig tissue samples after diffusion experiments; (A) photo of blank minipig tissue sample; (B-C) photos of minipig skin treated with F2 microneedle array containing nitrazine yellow indicator (blue dye); (D) microscope image of blank minipig tissue (10× mag); (E) microscope image of minipig skin treated with F1 microneedle array, no indicator (10× mag); (F) microscope image minipig skin treated with F1 microneedle array, no indicator (50× magn.)

A photograph of skin treated with formulation F2 microneedle shows array patterns in the skin with dark blue marks where microneedles penetrated skin (FIG. 6). Needle cavities, in minipig skin treated with F1 microneedles without nitrazine yellow indicator, were observed under the microscope (FIG. 6). FIG. 6 was produced with a light microscope (Swift-Duo Vision Engineering, Woking, UK) and imaging software (M3 Metrology, Vision Engineering, Woking, UK).

In a separate experiment, active transdermal diffusion of the API using iontophoresis (i.e. electric current) was measured across female minipig skins using microneedle arrays prepared from formulation F1. For iontophoresis samples, a 0.6 mA/cm$^2$ current was applied across an anode electrode located on the microneedle and a cathode electrode located in the franz cell receiver compartment. The cumulative amount (μg/cm2) of the drug, in the formulation, was recorded over an 8-hour period. For comparison, non-iontophoretic diffusion experiments with microneedle arrays were performed using the same lot of female minipig skin. An 8-hour period was selected as appropriate because most iontophoretic treatment regimens are less than 8 hours.

Data, including microneedle drug load (μg/cm2); cumulative amounts, Q (μg/cm2); percentage released at 8-hour; sumatriptan steady-state flux, Jss (μg/cm2 hr) and lag time (hr) were recorded or calculated (Table 4). The steady-state flux and the lag time (hr) were approximated for all experiments by taking the slope of the steady-state portion of the cumulative flux curves. The steady-state flux occurred in microneedle arrays and tape-stripped inverted samples within 4 to 8 hours.

| Sample | Sample Size | Drug Load (μg/cm$^2$) | Cumulative Amount, $Q_8$ (μg/cm$^2$) | Percentage Released in 24 h (%) |
|---|---|---|---|---|
| F1 Microneedle | n = 2 | 10338 ± 9.0 | 1832 ± 581 | 17.7 ± 5.6 |
| F1 Microneedle + iontophoresis | n = 3 | 10798 ± 371 | 2315 ± 476 | 21.5 ± 4.9 |

| Sample | Sample Size | Sumatriptan Flux, $J_{ss}$ (μg/cm$^2$h) | Lag Time (h) |
|---|---|---|---|
| F1 Microneedle | n = 2 | 274 ± 73 | 1.4 ± 0.37 |
| F1 Microneedle + iontophoresis | n = 3 | 305 ± 72 | 0.32 ± 0.34 |

Table 4 lists the sumatriptan succinate active diffusion data for the Franz cell experiments after 8 hours; average values ±SD; iontophoresis using electric current of 0.6 mA/cm$^2$.

All references disclosed herein are incorporated by reference. Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

The invention claimed is:

1. A method for the preparation of a polymeric microneedle array for delivery of macromolecular compounds through the skin having a plurality of micro-scaled solid dissolvable microneedles, each of the microneedles being entirely made of a dried polymer composition which is dissolvable upon contact with the skin, the polymer composition comprising:
   15 to 40 wt. % of a water soluble polymer as a binder, less than 2 wt. % of a humectant/softener, and
   less than 2 wt. % of a surfactant;
   and
   1 to 15 wt. % of the macromolecular compound encapsulated in the polymer, wherein the wt. % are given with respect to the liquid polymer composition before drying, said method comprising the steps of:
   dissolving
   15 to 40 wt. % of a water soluble polymer as a binder, less than 2 wt. % of a humectant/softener, and
   less than 2 wt. % of a surfactant, and
   1 to 15 wt. % of a macromolecular compound
   in water, to prepare a liquid polymer composition; wherein the wt. % are given with respect to the liquid polymer composition before drying;
   molding the liquid polymer composition in flexible molds having the negative form of the microarray to be produced;
   drying the polymer composition within the mold; and
   removing the dried polymeric having formed solid dissolvable microneedles from the mold;
   wherein the humectant and softener is present in the liquid polymer composition before drying in an amount of 0.5 to 1.5 wt. %.

2. The method of claim 1, wherein the water soluble polymer is polyvinylpyrrolidone (PVP).

3. The method of claim 2, wherein the water soluble polymer is a medium viscosity PVP having an average molecular weight (Mw) of about 40,000.

4. The method of claim 1, wherein the humectant and softener is glycerol.

5. The method of claim 1, wherein the surfactant is polysorbate 80.

6. The method of claim 1, wherein the macromolecular compound is hydrophilic.

7. The method of claim 1, wherein the macromolecular compound is sumatriptan or sumatriptan succinate.

8. The method of claim 1, wherein the water soluble polymer is present in the liquid polymer composition before drying in an amount of 20 to 30 wt. %.

9. The method of claim 1, wherein the surfactant is present in the liquid polymer composition before drying in an amount of 0.05 to 1.0 wt. %.

10. The method of claim 1, wherein the macromolecular compound is present in the liquid polymer composition before drying in an amount of 5 to 10 wt. %.

11. The method of claim 1, wherein the water soluble polymer is a medium viscosity PVP having an average molecular weight (Mw) of about 40,000.

12. The method of claim 1, wherein the micro-scaled solid dissolvable microneedles have a height of about 50 to 900 μm and a surface density of about 2,000 needles/cm$^2$ or less.

13. An active transdermal patch device for delivery of macromolecular compounds through the skin, comprising:
   a power supply with controllable current source,
   a skin cathode electrically connected to the power supply, and
   a skin anode electrically connected to the power supply, the anode comprising a microneedle array having a plurality of micro-scaled solid dissolvable microneedles, each of the microneedles being entirely made of a dried polymer composition which is dissolvable upon contact with the skin, the microneedle arrays being obtained by the method of claim 1.

14. A polymeric for delivery of macromolecular compounds through the skin having a plurality of micro-scaled solid dissolvable microneedles, the microneedles consisting of a dried polymer composition which a water soluble consists of polymer, a humectant softener, a surfactant, and the encapsulated macromolecular compound, and wherein the polymeric is obtained by the method of claim 1.

15. A polymeric for delivery of macromolecular compounds through the skin having a plurality of micro-scaled solid dissolvable microneedles, each of the microneedles being entirely made of a dried polymer composition which is dissolvable upon contact with the skin, the polymeric microneedle array being obtained by the method of claim 1.

\* \* \* \* \*